(12) United States Patent
Steudel

(10) Patent No.: US 8,404,361 B2
(45) Date of Patent: Mar. 26, 2013

(54) ELECTROLUMINESCENT MATERIAL AND DEVICE

(75) Inventor: Annette Steudel, Cambridge (GB)

(73) Assignees: Cambridge Display Technology Limited, Cambridgeshire (GB); Sumitomo Chemical Co., Limited, Tokyo (JP)

( * ) Notice: Subject to any disclaimer, the term of this patent is extended or adjusted under 35 U.S.C. 154(b) by 502 days.

(21) Appl. No.: 12/533,886

(22) Filed: Jul. 31, 2009

(65) Prior Publication Data

US 2010/0029886 A1 Feb. 4, 2010

(30) Foreign Application Priority Data

Sep. 2, 2008 (GB) .................... 0815953.5

(51) Int. Cl.
*B32B 9/04* (2006.01)
*B32B 19/04* (2006.01)
*C08G 79/08* (2006.01)
*C08G 73/02* (2006.01)
*C08G 61/00* (2006.01)

(52) U.S. Cl. ............ 428/690; 428/917; 528/8; 528/396; 528/397

(58) Field of Classification Search .................. 428/690, 428/917; 528/8, 396, 397
See application file for complete search history.

(56) References Cited

U.S. PATENT DOCUMENTS

| | | | |
|---|---|---|---|
| 5,621,131 A | 4/1997 | Kreuder et al. | |
| 5,723,873 A | 3/1998 | Yang | |
| 5,798,170 A | 8/1998 | Zhang et al. | |
| 6,268,695 B1 | 7/2001 | Affinito | |
| 6,383,083 B1 | 5/2002 | Johnston | |
| 2004/0109955 A1 | 6/2004 | Kitano et al. | |
| 2004/0209118 A1 | 10/2004 | Seo et al. | |

FOREIGN PATENT DOCUMENTS

| | | |
|---|---|---|
| EP | 0707020 A2 | 4/1997 |
| EP | 0949850 A1 | 3/1998 |
| EP | 0842208 A1 | 5/1998 |
| EP | 0880303 A1 | 11/1998 |
| EP | 0901176 A2 | 3/1999 |
| EP | 0947123 A1 | 10/1999 |
| GB | 2348316 A | 9/2000 |
| JP | 2000315580 A | 11/2000 |
| JP | 2006253251 A | 9/2006 |
| WO | WO-9857381 A1 | 2/1998 |
| WO | WO-9810621 A1 | 3/1998 |
| WO | WO-9948160 A1 | 9/1999 |
| WO | WO-0053656 A1 | 4/2000 |
| WO | WO-0048258 A1 | 8/2000 |
| WO | WO 0055927 A1 | 9/2000 |
| WO | WO-0119142 A1 | 3/2001 |
| WO | WO-0181649 A1 | 11/2001 |
| WO | WO-02084759 A1 | 10/2002 |
| WO | WO-2005049546 A1 | 6/2005 |

(Continued)

OTHER PUBLICATIONS

Search Report for Application No. for GB0815953.5, dated Jan. 9, 2009.

(Continued)

*Primary Examiner* — Duc Truong

(74) *Attorney, Agent, or Firm* — Marshall, Gerstein & Borun LLP

(57) ABSTRACT

A device comprising an electroluminescent copolymer comprising a light-emitting repeat unit in the polymer backbone and wherein the repeat unit is conjugatively separate from the polymer backbone.

26 Claims, 1 Drawing Sheet

FOREIGN PATENT DOCUMENTS

| | | |
|---|---|---|
| WO | WO-2006/070184 A1 | 7/2006 |
| WO | WO-2008/150828 A2 | 12/2008 |

OTHER PUBLICATIONS

Bernius et al., "Progress with Light-Emitting Polymers," *Adv. Mater.*, 12:1737-1750 (2000).

Ferreira et al., "Novel synthetic routes to thienocarbazoles via palladium or copper catalyzed amination or amidation of arylhalides and intramolecular cyclization," *Tetrahedron*, 58:7943-7949 (2002).

Niu et al., "Thermal annealing below the glass transition temperature: A general way to increase performance of light-emitting diodes based on copolyfluorenes," *Applied Physics Letters*, 81:634-636 (2002).

Setayesh et al., "Bridging the Gap between Polyfluorene and Ladder-Poly-p-phenylene: Synthesis and Characterization of Poly-2,8-indenofluorene," *Macromolecules*, 33:2016-2020 (2000).

Wolfe et al., "Palladium-Catalyzed Amination of Aryl Halides and Aryl Triflates: N-Hexyl-2-Methyl-4-Methoxyaniline and N-Methyl-N-(4-Chlorophenyl) Aniline," *Organic Syntheses*, 10:423 (2004); 78:23 (2002).

Yamaguchi et al., "Effects of B and C on the Ordering of $L1_0$-CoPt thin films," *Applied Physics Letters*, 79:2001-2003 (2001).

Yamamoto, "Electrically Conducting and Thermally Stable $\pi$-Conjugated Poly (arylene)s Prepared by Organometallic Processes," *Prog. Polym. Sci.*, 17:1153-1205 (1992).

Yang, "Efficient blue polymer light-emitting diodes from a series of soluble poly(paraphenylene)s," *J. Appl. Phys.*, 79:934-939 (1996).

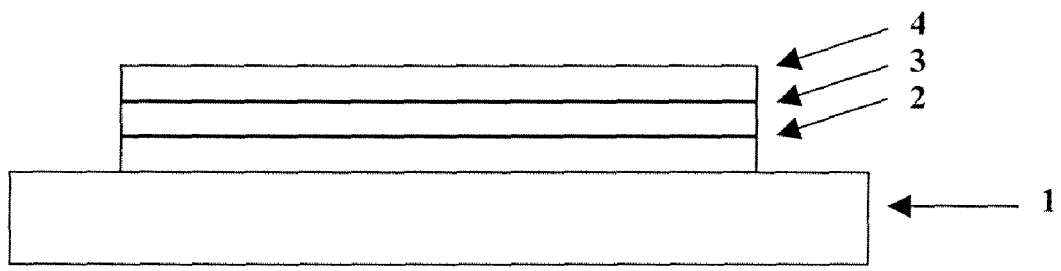

ELECTROLUMINESCENT MATERIAL AND DEVICE

FIELD OF THE INVENTION

The invention relates to electroluminescent materials for use in optical devices, polymeric electroluminescent materials and to devices incorporating such materials.

BACKGROUND OF THE INVENTION

It is known that certain small molecules can emit, by fluorescence, visible green light. One such molecule is disclosed as Chemical formula 1 in US 2004/0209118 A1.

It is also know to incorporate small molecules into a polymer backbone via para-linked amine repeat units, as is shown in WO 2005/049546. The polymers formed using the disclosure of WO 2005/049546 are said to afford devices incorporating the same with longer lifetimes.

When incorporating the small molecule of US 2004/0209118 A1 into a polymeric backbone according to the teaching of WO 2005/049546 there is a significant reduction in luminescent quantum yield and quantum efficiency.

SUMMARY OF THE INVENTION

The invention provides a further light emissive species which provides a required color while showing good efficiency and lifetime, preferably better, than those known to date.

The invention also provides a soluble green emitting polymer (the term "green emitting polymer" means a polymer that emits light in the range of 500-580 nm, preferably 510-550 nm, as measured by photoluminescence).

In one aspect the invention provides a device comprising an electroluminescent copolymer comprising a visible light emitting repeat unit in the polymer backbone and wherein the repeat unit is conjugatively separate from the polymer backbone.

Other aspects of the invention relate to white light emitting devices and organic light-emitting diodes (OLEDs) incorporating copolymers according to the invention.

As used herein the terms "conjugatively separate", "conjugatively separated" and similar terms are intended to mean that there is no possibility of conjugation between an emitting region and a further region, such as a polymeric backbone, to which it is attached.

BRIEF DESCRIPTION OF THE DRAWINGS

So that the invention may be more fully understood it will now be described, by way of example only, and with reference to the examples and accompanying drawings, in which:

FIG. 1 is a schematic representation of an organic electroluminescent device according to the invention.

GENERAL DESCRIPTION OF THE INVENTION

The invention provides a device comprising an electroluminescent copolymer comprising a light-emitting repeat unit in a polymer backbone and wherein the repeat unit is conjugatively separate from the polymer backbone. Preferably, the electroluminescent copolymer has a luminescence emission maximum between 500 nm and 580 nm, preferably between 510 nm and 560 nm.

Preferably, the light-emitting repeat unit is conjugatively separated from the polymer backbone by at least one of: a twisting unit; meta linkages; and non-conjugating spacers. Highly preferably, the light-emitting repeat unit is conjugatively separated from the polymer backbone by an alkyl phenylene unit, preferably a 1,4 alkylphenylene unit. In this embodiment, the light-emitting repeat unit preferably is conjugatively separated from the polymer backbone by:

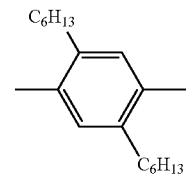

In one embodiment, the light-emitting repeat unit is conjugatively separated from the polymer backbone by an ether linkage.

Preferably, the light-emitting repeat unit comprises:

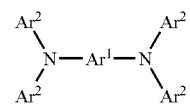

wherein $Ar^1$ is a fused aromatic or hetero aromatic ring and each $Ar^2$ is an aromatic or hetero aromatic ring. In this embodiment, at least one of each $Ar^2$ preferably is a substituted aromatic or hetero aromatic ring, and highly preferably an alkyl benzene. At least one of the aromatic or hetero aromatic rings $Ar^2$ may be fused.

In this embodiment, at least one of the aromatic or hetero aromatic rings $Ar^1$, $Ar^2$ may comprise a naphthalene group, and preferably an anthracene group.

In one embodiment, the copolymer has the form:

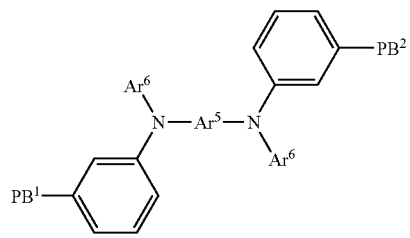

wherein $Ar^5$ and $Ar^6$ comprise optionally substituted aryl systems and $PB^1$ and $PB^2$ is the polymer backbone or one of $PB^1$ and $PB^2$ is the polymer backbone and the other is a terminating group.

In another embodiment, the copolymer has the form

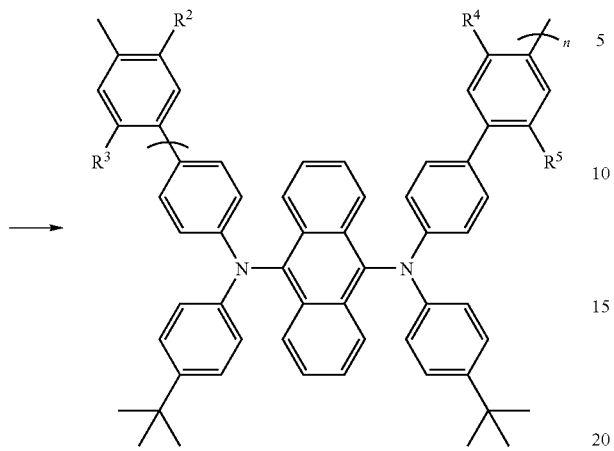

wherein $R^2$ to $R^5$ are the same or different and are selected from the group consisting of optionally substituted alkyl, alkoxy or aryl, and wherein $R^2$, $R^3$, $R^4$ and $R^5$ may be alkyl groups or at least partially substituted alkyl groups, such as $C_6H_{13}$ or longer alkyl groups, for example.

The light-emitting repeat unit preferably is present in a range of from above 0 wt % to 10 wt %, preferably from 1 wt % to 9 wt %, and most preferably from 2 wt % to 5 wt %.

Preferably, a full color organic light-emitting (OLED) display comprises a green- or white-emitting device according to the invention.

A method of fabricating a monomer for inclusion as an emitting region of a copolymer, in which the emitting region is conjugatively separate from the polymeric backbone preferably comprises the following synthesis:

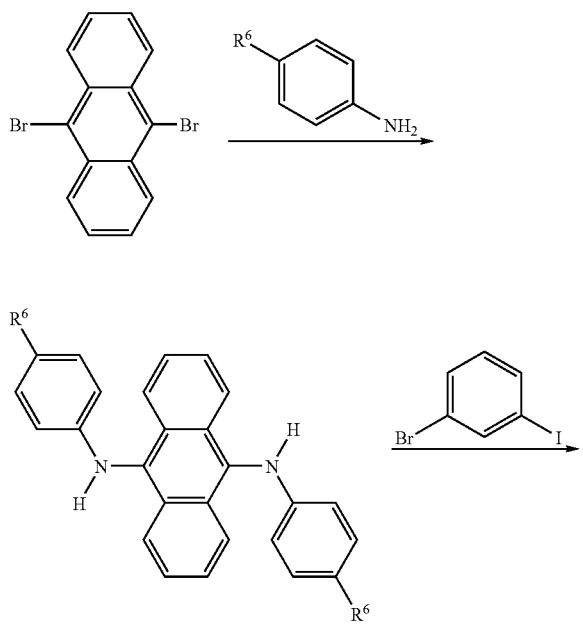

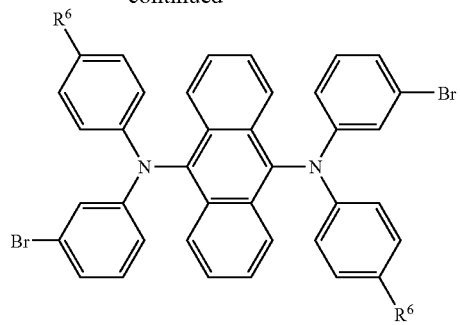

where each $R^6$ is an alkyl group or a substituted alkyl group.

DETAILED DESCRIPTION OF THE INVENTION

With reference to FIG. 1, the architecture of an electroluminescent device according to the invention comprises a transparent glass or plastic substrate 1, an anode 2 of indium tin oxide, and a cathode 4. An electroluminescent layer 3 is provided between the anode 2 and the cathode 4.

In a practical device, at least one of the electrodes is semi-transparent in order that light may be emitted. Where the anode is transparent, it typically comprises indium tin oxide ("ITO").

Further layers may be located between the anode 2 and the cathode 4, such as charge transporting, charge injecting, or charge blocking layers.

In particular, it is desirable to provide a conductive hole injection layer formed of a doped organic material located between the anode 2 and the electroluminescent layer 3 to assist hole injection from the anode into the layer or layers of semiconducting polymer. Examples of doped organic hole injection materials include poly(ethylene dioxythiophene) (PEDT), polyaniline as disclosed in U.S. Pat. No. 5,723,873 and U.S. Pat. No. 5,798,170, and poly(thienothiophene). Exemplary acids include PEDT doped with polystyrene sulfonate (PSS) as disclosed in EP 0901176 and EP 0947123, polyacrylic acid or a fluorinated sulfonic acid, for example Nafion®.

If present, a hole transporting layer located between the anode 2 and electroluminescent layer 3 preferably has a highest-occupied molecular orbital (HOMO) level of less than or equal to 5.5 eV, more preferably around 4.8 eV to 5.5 eV.

If present, an electron transporting layer located between the electroluminescent layer 3 and the cathode 4 preferably has a lowest unoccupied molecular orbital (LUMO) level of around 3 eV to 3.5 eV.

The electroluminescent layer 3 may consist of the electroluminescent copolymer of the invention alone or may comprise the electroluminescent copolymer in combination with one or more further materials. In particular, the electroluminescent material may be blended with hole and/or electron transporting materials as disclosed in, for example, WO 99/48160. Alternatively, the electroluminescent copolymer may be covalently bound to a charge transporting material and/or host material.

The electroluminescent layer 3 may be patterned or unpatterned. A device comprising an unpatterned layer may be used an illumination source, for example. A device comprising a patterned layer may be, for example, an active matrix display or a passive matrix display. In the case of an active matrix display, a patterned electroluminescent layer is typically used in combination with a patterned anode layer and an unpatterned cathode. In the case of a passive matrix display, the anode layer is formed of parallel stripes of anode material, and parallel stripes of electroluminescent material and cathode material arranged perpendicular to the anode material wherein the stripes of electroluminescent material and cathode material are typically separated by stripes of insulating material ("cathode separators") formed by photolithography.

The cathode 4 preferably is selected from materials that have a work function allowing injection of electrons into the electroluminescent layer. Other factors influence the selection of the cathode such as the possibility of adverse interactions between the cathode and the electroluminescent material. The cathode may consist of a single material such as a layer of aluminum. Alternatively, it may comprise a plurality of metals, for example a bilayer of a low work function material and a high work function material such as calcium and aluminum as disclosed in WO 98/10621; elemental barium as disclosed in WO 98/57381, Appl. Phys. Lett. 2002, 81(4), 634 and WO 02/84759; or a thin layer of metal compound, in particular an oxide or fluoride of an alkali or alkali earth metal, to assist electron injection, for example lithium fluoride as disclosed in WO 00/48258 or barium fluoride as disclosed in Appl. Phys. Left. 2001, 79(5), 2001. In order to provide efficient injection of electrons into the device, the cathode preferably has a work function of less than 3.5 eV, more preferably less than 3.2 eV, most preferably less than 3 eV.

The cathode may be opaque or transparent. Transparent cathodes are particularly advantageous for active matrix devices because emission through a transparent anode in such devices is at least partially blocked by drive circuitry located underneath the emissive pixels. A transparent cathode preferably will comprise a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

A transparent cathode device need not have a transparent anode (unless, of course, a fully transparent device is desired), and so the transparent anode used for bottom-emitting devices may be replaced or supplemented with a layer of reflective material such as a layer of aluminum. Examples of transparent cathode devices are disclosed in, for example, GB 2348316.

Optical devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

The device is preferably encapsulated with an encapsulant (not shown) to prevent ingress of moisture and oxygen. Suitable encapsulants include a sheet of glass, films having suitable barrier properties such as alternating stacks of polymer and dielectric as disclosed in, for example, WO 01/81649 or an airtight container as disclosed in, for example, WO 01/19142. A better material for absorption of any atmospheric moisture and/or oxygen that may permeate through the substrate or encapsulant may be disposed between the substrate and the encapsulant.

The embodiment of FIG. 1 illustrates a device wherein the device is formed by firstly forming an anode on a substrate followed by deposition of an electroluminescent layer and a cathode, however it will be appreciated that the device of the invention could also be formed by firstly forming a cathode on a substrate followed by deposition of an electroluminescent layer and an anode.

The electroluminescent copolymer preferably comprises an arylene repeat unit as disclosed in, for example, Adv. Mater. 2000 12(23) 1737-1750 and references therein. Exemplary arylene repeat units include: 1,4-phenylene repeat units as disclosed in J. Appl. Phys. 1996, 79, 934; fluorene repeat units as disclosed in EP 0842208; indenofluorene repeat units as disclosed in, for example, Macromolecules 2000, 33(6), 2016-2020; and spirofluorene repeat units as disclosed in, for example EP 0707020. Each of these repeat units is optionally substituted. Examples of substituents include solubilizing groups such as $C_{1-20}$ alkyl or alkoxy; electron withdrawing groups such as fluorine, nitro or cyano; and substituents for increasing glass transition temperature (Tg) of the polymer.

Particularly preferred polymers comprise optionally substituted, 2,7-linked fluorenes, most preferably repeat units of formula VIII:

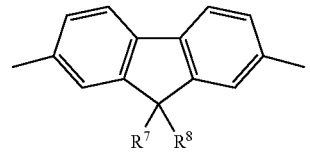

(VIII)

wherein $R^7$ and $R^8$ are independently selected from hydrogen or optionally substituted alkyl, alkoxy, aryl, arylalkyl, heteroaryl and heteroarylalkyl. More preferably, at least one of $R^7$ and $R^8$ comprises an optionally substituted $C_4$-$C_{20}$ alkyl or aryl group. In the case where $R^7$ and/or $R^8$ is alkyl, one or more non-adjacent C atoms of the alkyl group other that the C atom adjacent to the fluorene group may be replaced with O, S, N, C=O or —COO—. In the case where $R^7$ and/or $R^8$ is aryl, arylalkyl, heteroaryl or heteroarylalkyl, optional substituents are preferably selected from alkyl, alkoxy, alkylthio, fluorine, cyano, aralykyl, CHO, and $CO_2H$ or an ester thereof. In one preferred embodiment, the electroluminescent copolymer comprises more than one repeat unit of formula (VIII), for example a repeat unit of formula (VIII) comprising alkyl substituents and a repeat unit of formula (VIII) comprising optionally substituted aryl or heteroaryl substituents.

The electroluminescent copolymer preferably comprises a triarylamine repeat unit of formula (IX) to provide hole transport, and is preferably used in combination with an arylene repeat as described.

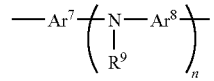

(IX)

wherein $Ar^7$ and $Ar^8$ are optionally substituted aryl or heteroaryl groups, n is greater than or equal to 1, preferably 1 or 2, and $R^9$ is H or a substituent, preferably a substituent. $R^9$ is preferably alkyl or aryl or heteroaryl, most preferably aryl or heteroaryl. Any of the aryl or heteroaryl groups in the unit of formula 1 may be substituted. Preferred substituents include alkyl and alkoxy groups. Any of the aryl or heteroaryl groups in the repeat unit of Formula 1 may be linked by a direct bond or a divalent linking atom or group. Preferred divalent linking atoms and groups include O, S; substituted N; and substituted C.

Particularly Preferred Units Satisfying Formula (IX) Include Units of Formulae 1-3:

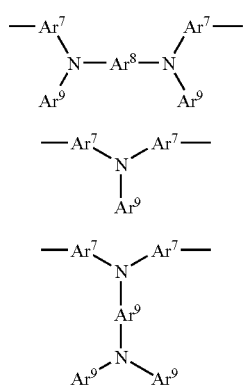

wherein $Ar^7$ and $Ar^8$ are as defined above; and $Ar^9$ is optionally substituted aryl or heteroaryl. Where present, preferred substituents for $Ar^9$ include alkyl and alkoxy groups.

The hole-transporting repeat units of formula (IX) are preferably present in an amount up to 20 mol %, more preferably up to 10 mol % or even up to 5 mol %. More than one hole-transporting unit may be present in the polymer; in one preferred embodiment the polymer comprises repeat units of both formulae 1 and 2.

The electroluminescent copolymer may comprise an electroluminescent region comprising the light-emitting repeat unit and at least one of a hole transporting region and an electron transporting region as disclosed in, for example, WO 00/55927 and U.S. Pat. No. 6,353,083. If only one of a hole transporting region and electron transporting region is provided then the electroluminescent region may also provide the other of hole transport and electron transport functionality.

Preferred methods for preparation of these polymers are Suzuki polymerization as described in, for example, WO 00/53656 and Yamamoto polymerisation as described in, for example, T. Yamamoto, "Electrically Conducting And Thermally Stable π—Conjugated Poly(arylene)s Prepared by Organometallic Processes", Progress in Polymer Science 1993, 17, 1153-1205. These polymerization techniques both operate via a "metal insertion" wherein the metal atom of a metal complex catalyst is inserted between an aryl group and a leaving group of a monomer. In the case of Yamamoto polymerization, a nickel complex catalyst is used; in the case of Suzuki polymerization, a palladium complex catalyst is used.

For example, in the synthesis of a linear polymer by Yamamoto polymerization, a monomer having two reactive halogen groups is used. Similarly, according to the method of Suzuki polymerization, at least one reactive group is a boron derivative group such as a boronic acid or boronic ester and the other reactive group is a halogen. Preferred halogens are chlorine, bromine and iodine, most preferably bromine.

Repeat units and end groups comprising aryl groups as illustrated throughout this application may be derived from a monomer carrying a suitable leaving group.

Suzuki polymerization may be used to prepare regioregular, block, and random copolymers. In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

As alternatives to halides, other leaving groups capable of participating in metal insertion include groups include tosylate, mesylate and triflate.

A single polymer or a plurality of polymers may be deposited from solution to form layer 5. Suitable solvents for polyarylenes, in particular polyfluorenes, include mono- or poly-alkylbenzenes such as toluene and xylene. Particularly preferred solution deposition techniques are spin-coating and inkjet printing.

Spin-coating is particularly suitable for devices wherein patterning of the electroluminescent material is unnecessary—for example for lighting applications or simple monochrome segmented displays.

Inkjet printing is particularly suitable for high information content displays, in particular full color displays. Inkjet printing of OLEDs is described in, for example, EP 0880303.

Other solution deposition techniques include dip-coating, roll printing, and screen printing.

If multiple layers of the device are formed by solution processing then the skilled person will be aware of techniques to prevent intermixing of adjacent layers, for example by crosslinking of one layer before deposition of a subsequent layer or selection of materials for adjacent layers such that the material from which the first of these layers is formed is not soluble in the solvent used to deposit the second layer.

The electroluminescent copolymer of the invention may have any color of emission in the visible spectrum.

In the case of a red emitter, it preferably has an emission peak in the range of 600 nm-750 nm, preferably 600 nm-700 nm, more preferably 610 nm-650 nm and most preferably having an emission peak around 650 nm-660 nm.

In the case of a green emitter, it preferably has an emission peak in the range of 510 nm-560 nm.

In the case of a blue emitter, it preferably has an emission peak in the range of 400 nm-500 nm, more preferably 430 nm-500 nm.

In the case of a yellow emitter, it preferably has an emission peak in the range of 560 nm-580 nm.

The emission peaks referred to above are emission peaks are photoluminescent emission peaks.

Comparative Example 1

The molecule (I) below is blended with a polymer comprising fluorene repeat units of formula (VIII), amine repeat units of formula (1) and as described in US 2004/109955 A1 and N-phenylphenoxazine repeat units. The molecule is blended at a level of 4.6 w/w %. Molecule (I) is disclosed in US 2004/0209118 A1:

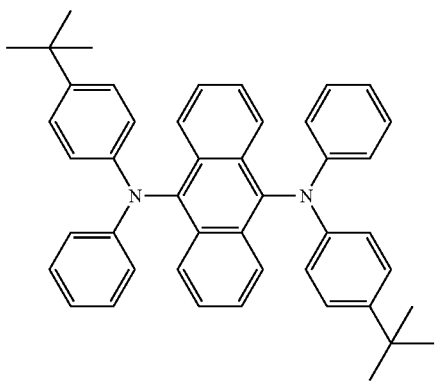

(I)

Comparative Example 2

A polymer comprising fluorene repeat units of formula (VIII), amine repeat units of formula (1) and as described in US 2004/109955 A1, N-phenylphenoxazine repeat units and a green emitting repeat unit derived from the monomer of formula (II) below as described in WO 2005/049546 was prepared by Suzuki polymerization as disclosed in WO 00/53656. The repeat unit derived from the monomer of formula (II) is conjugatively linked to the polymer backbone by virtue of its para-linkage.

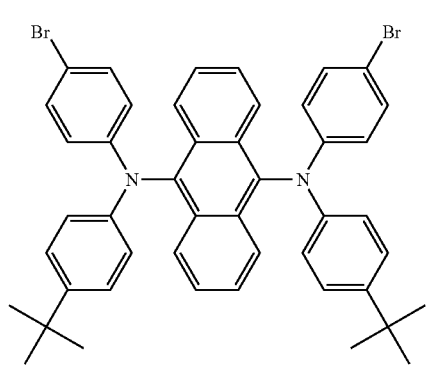

(II)

Example 1

The following synthesis was carried out

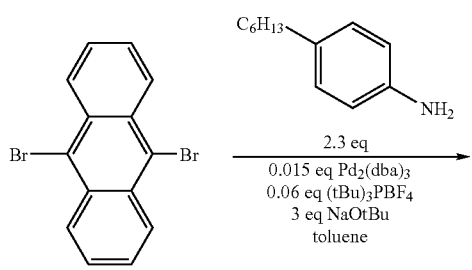

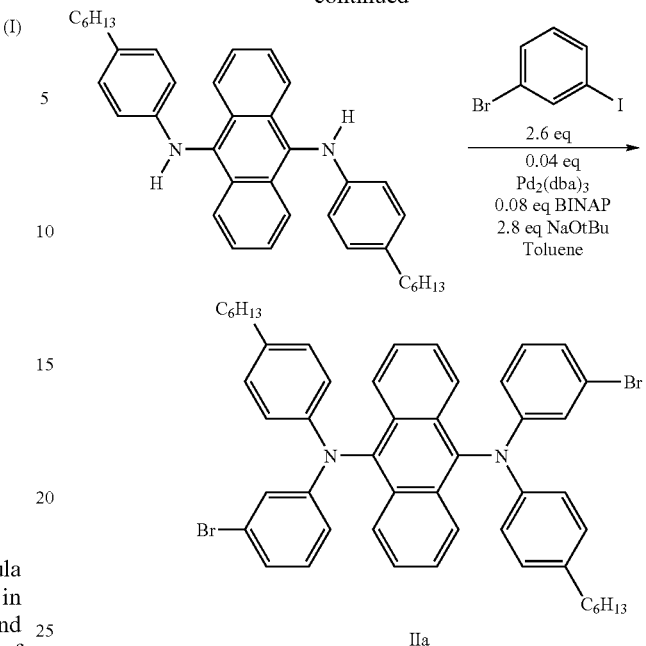

9,10-dibromoanthracene and 4-n-hexylaniline were reacted using common Buchwald conditions (for example see J. P. Wolfe, S. L. Buchwald, *Organic Syntheses*, Coll. Vol. 10, p. 423 (2004)). For the selective coupling reaction conditions were used as described in I. C. F. R. Ferreira, M-J. R. P. Queiroz, G. Kirsch, *Tetrahedron*, 2002, 58, 7943-7949. The structure was confirmed by NMR and LCMS.

The Br substituents are located at the meta positions of the benzene rings. The synthesis occurs in only two steps.

A polymer was prepared as per Comparative Example 2, except that the polymer comprises repeat units of formula (IIa) instead of repeat units of formula (II) at a level of 3 mol %.

Example 2

In order to demonstrate another means for conjugatively isolating the green emitting unit from the polymeric backbone, a repeat unit based on monomer (II) of Comparative Example 2 was incorporated into a polymeric backbone by polymerising 50 mol % of a twisting monomeric unit TW1 (illustrated below) in combination with fluorene repeat units of formula (VIII), amine repeat units of formula (1) and as described in US 2004/109955 A1, and N-phenylphenoxazine repeat units.

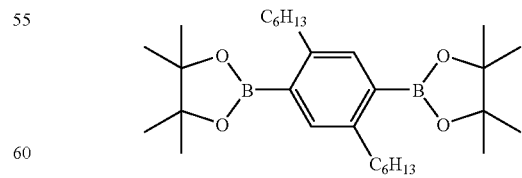

Clearly, other twisting units will be known to the skilled addressee.

Without wishing to be bound by any particular theory it is postulated that the presence of large groups such as alkyl groups (in particular ethyl or higher), and optionally substituted aromatic groups (in particular mono-poly-alkyl substituted phenyl) induces steric hindrance, so as to cause or provide a twist, and alkyl groups, where present, impart solubility to the polymer.

Example 3

A polymer comprising fluorene repeat units of formula (VIII); N-octylphenoxazine repeat units; and repeat units derived from monomer (III) below was prepared by Suzuki polymerization:

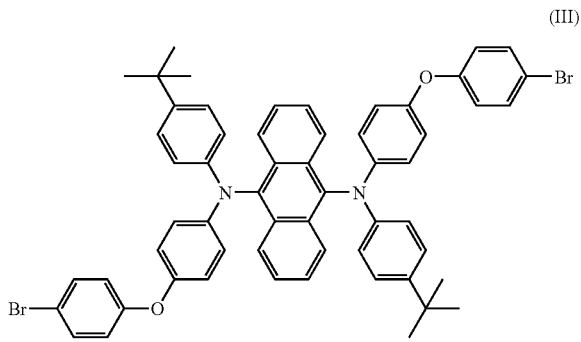

(III)

Other non conjugating spacers may be used to separate compounds of I from a polymer backbone, such as those disclosed as II and III in WO 05/013386 (the entire disclosure of which is herein incorporated by reference).

The photoluminescence quantum yield (PLQY) of the compounds and compositions of the Examples and Comparative Examples were measured, and the results are provided in Table 1:

TABLE 1

| Example | PLQY/% | λmax (nm) |
|---|---|---|
| Comparative Example 1 | 69 | 516 |
| Comparative Example 2 | 45 | 532 |
| Example 1 | 95 | 525 |
| Example 2 | 75 | 532 |
| Example 3 | 89 | 533 |

As can be seen from these results, the polymers of the invention comprising an emissive unit that has been conjugatively separated from the rest of the polymer has a higher PLQY than either Comparative Example 1 (blend of small molecule emitter and polymer) or Comparative Example 2 (emitting repeat unit conjugatively linked to adjacent repeat units).

The polymers of Example 1, Comparative Example 2, and the Comparative Examples were used as the electroluminescent layer of a light emitting device comprising, in sequence:
ITO anode;
Hole injecting layer of PEDT/PSS;
Hole transporting layer comprising fluorene repeat units and amine repeat units;
Electroluminescent layer; and
Cathode bilayer of BaO/Al.

The external quantum efficiencies (EQEs) of the devices comprising Example 1 and Comparative Example 2 were, respectively, 4.74% and 3.78%—that is, the EQE of the polymer according to the invention is about 25% higher than that of the comparative polymer.

By conjugatively isolating the emissive unit from the polymeric backbone it is possible to provide a soluble emitter which has good color, a high lifetime, and good efficiency.

Other conjugation breaks could be used as would be understood by the skilled addressee.

The invention claimed is:

1. A device comprising an electroluminescent copolymer comprising a light-emitting repeat unit in a polymer backbone wherein the repeat unit is conjugatively separate from the polymer backbone.

2. A device according to claim 1 wherein the electroluminescent copolymer has a luminescence emission maximum between 500 nm and 580 nm.

3. A device according to claim 1, wherein the light-emitting repeat unit is conjugatively separated from the polymer backbone by at least one of:
a twisting unit;
meta linkages; and
non-conjugating spacers.

4. A device according to claim 3, wherein the light-emitting repeat unit is conjugatively separated from the polymer backbone by an alkyl phenylene unit.

5. A device according to claim 4, wherein the light-emitting repeat unit is conjugatively separated from the polymer backbone by:

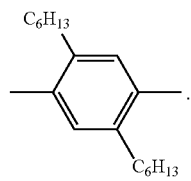

6. A device according to claim 3, wherein the light-emitting repeat unit is conjugatively separated from the polymer backbone by an ether linkage.

7. A device according to claim 1, wherein the light-emitting repeat unit comprises:

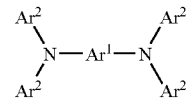

wherein $Ar^1$ is a fused aromatic or hetero aromatic ring and each $Ar^2$ is an aromatic or hetero aromatic ring.

8. A device according to claim 7, wherein at least one of each $Ar^2$ is a substituted aromatic or hetero aromatic ring.

9. A device according to claim 8, wherein at least one of each $Ar^2$ is an alkyl benzene.

10. A device according to claim 7, wherein at least one of the aromatic or hetero aromatic rings $Ar^2$ is fused.

11. A device according to claim 7, wherein at least one of the aromatic or hetero aromatic rings $Ar^1$, $Ar^2$ comprises a naphthalene group.

12. A device according to claim 7, wherein $Ar^1$ comprises an anthracene group.

13. A device according to claim 7, wherein the copolymer has the form:

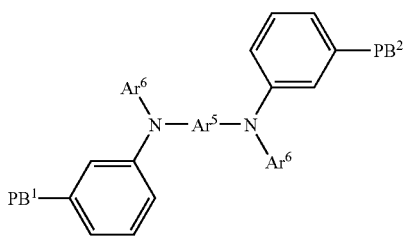

wherein Ar[5] and Ar[6] comprise optionally substituted aryl systems and PB[1] and PB[2] is the polymer backbone or one of PB[1] and PB[2] is the polymer backbone and the other is a terminating group.

14. A device according to claim 7, wherein the copolymer has the form

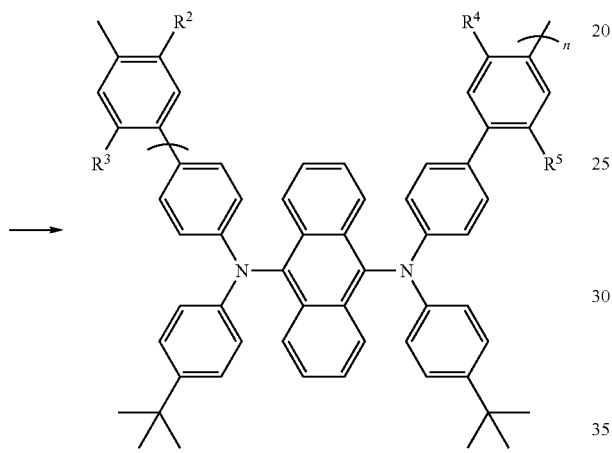

wherein R[2] to R[5] are the same or different and are selected from the group consisting of optionally substituted alkyl, alkoxy, and aryl.

15. A device according to claim 14, wherein at least one of R[2], R[3], R[4] and R[5] is an alkyl group or an at least partially substituted alkyl group.

16. A device according to claim 15, wherein the alkyl groups are $C_6H_{13}$ or longer alkyl groups.

17. A device according to claim 1, wherein the light-emitting repeat unit is present in a range of from above 0 wt % to 10 wt %.

18. A full color organic light-emitting (OLED) display comprising a green emitting device according to claim 1.

19. A white light emitting device comprising a device as claimed in claim 1.

20. A method of fabricating a monomer for inclusion as an emitting region of a copolymer, in which the emitting region is conjugatively separate from the polymeric backbone, the method comprising the steps of the following synthesis:

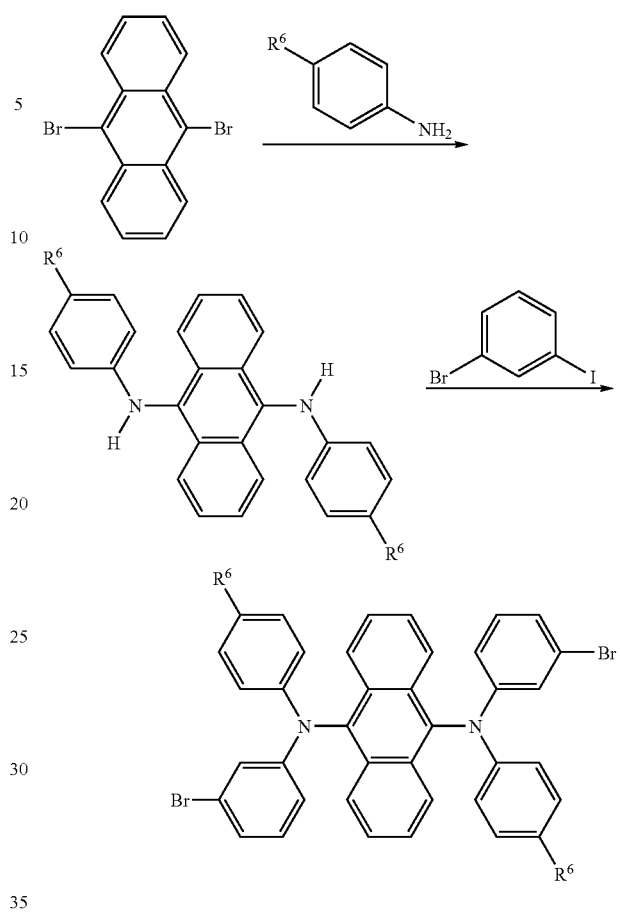

where each R[6] is an alkyl group or a substituted alkyl group.

21. A device according to claim 1 wherein the electroluminescent copolymer has a luminescence emission maximum between 510 nm and 560 nm.

22. A device according to claim 3, wherein the light-emitting repeat unit is conjugatively separated from the polymer backbone by a 1,4 alkylphenylene unit.

23. A device according to claim 1, wherein the light-emitting repeat unit is present in a range of from 1 wt % to 9 wt %.

24. A device according to claim 1, wherein the light-emitting repeat unit is present in a range of from 2 wt % to 5 wt %.

25. A device according to claim 1, wherein the light-emitting repeat unit is conjugatively separated from the polymer backbone by meta linkages.

26. A device according to claim 1, wherein the light-emitting repeat unit is conjugatively separated from the polymer backbone by non-conjugating spacers.

* * * * *